(12) United States Patent
Furst

(10) Patent No.: US 8,016,881 B2
(45) Date of Patent: Sep. 13, 2011

(54) SUTURES AND SURGICAL STAPLES FOR ANASTAMOSES, WOUND CLOSURES, AND SURGICAL CLOSURES

(75) Inventor: Joseph G. Furst, Lyndhurst, OH (US)

(73) Assignee: ICON Interventional Systems, Inc., Cleveland, OH (US)

( * ) Notice: Subject to any disclaimer, the term of this patent is extended or adjusted under 35 U.S.C. 154(b) by 1929 days.

(21) Appl. No.: 10/935,516

(22) Filed: Sep. 7, 2004

(65) Prior Publication Data

US 2005/0038472 A1   Feb. 17, 2005

Related U.S. Application Data

(63) Continuation-in-part of application No. 10/209,591, filed on Jul. 31, 2002, now abandoned.

(60) Provisional application No. 60/567,702, filed on May 3, 2004.

(51) Int. Cl.
*A61F 2/06* (2006.01)
*A61B 17/04* (2006.01)

(52) U.S. Cl. .................. 623/1.46; 428/423.1; 424/486

(58) Field of Classification Search .............. 623/1.46, 623/1.47, 1.48, 1.49; 424/468, 486, 354; 428/423.1, 423.7, 424.8
See application file for complete search history.

(56) References Cited

U.S. PATENT DOCUMENTS

| | | | |
|---|---|---|---|
| 4,043,344 A * | 8/1977 | Landi et al. ............ 606/230 |
| 4,739,762 A | 4/1988 | Palmaz |
| 4,773,665 A | 9/1988 | Hindle |
| 4,776,337 A | 10/1988 | Palmaz |
| 4,841,068 A | 6/1989 | Fujikawa et al. |
| 4,888,389 A | 12/1989 | Kennedy et al. |
| 4,942,204 A | 7/1990 | Kennedy |
| 5,024,671 A | 6/1991 | Tu et al. |
| 5,037,392 A | 8/1991 | Hillstead |
| 5,051,272 A | 9/1991 | Hermes et al. |
| 5,059,166 A | 10/1991 | Fishell et al. |
| 5,067,491 A | 11/1991 | Taylor, II et al. |
| 5,073,381 A | 12/1991 | Ivan et al. |
| 5,102,417 A | 4/1992 | Palmaz |
| 5,108,424 A | 4/1992 | Hoffman, Jr. et al. |
| 5,116,318 A | 5/1992 | Hillstead |
| 5,180,366 A | 1/1993 | Woods |
| 5,185,408 A | 2/1993 | Tang et al. |
| 5,195,984 A | 3/1993 | Schatz |
| 5,197,977 A | 3/1993 | Hoffman, Jr. et al. |
| 5,246,452 A | 9/1993 | Sinnott |
| 5,283,257 A | 2/1994 | Gregory et al. |
| 5,304,121 A | 4/1994 | Sahatjian |
| 5,306,250 A | 4/1994 | March et al. |
| 5,316,023 A | 5/1994 | Palmaz |
| 5,344,426 A | 9/1994 | Lau et al. |
| 5,370,681 A | 12/1994 | Herweck et al. |
| 5,383,927 A | 1/1995 | De Goicoechea et al. |
| 5,383,928 A | 1/1995 | Scott et al. |
| 5,417,981 A | 5/1995 | Endo et al. |
| 5,443,498 A | 8/1995 | Fontaine |
| 5,449,382 A | 9/1995 | Dayton |
| 5,464,650 A | 11/1995 | Berg et al. |
| 5,500,013 A | 3/1996 | Buscemi et al. |
| 5,516,781 A | 5/1996 | Morris et al. |
| 5,540,773 A | 7/1996 | Chesterfield et al. |
| 5,545,208 A | 8/1996 | Wolff et al. |
| 5,563,056 A | 10/1996 | Swan et al. |
| 5,563,146 A | 10/1996 | Morris et al. |
| 5,571,170 A | 11/1996 | Palmaz |
| 5,578,075 A | 11/1996 | Dayton |
| 5,605,696 A | 2/1997 | Eury et al. |
| 5,609,629 A | 3/1997 | Fearnot et al. |
| 5,616,608 A | 4/1997 | Kinsella et al. |
| 5,624,411 A | 4/1997 | Tuch |
| 5,649,977 A | 7/1997 | Campbell |
| 5,665,728 A | 9/1997 | Morris et al. |
| 5,679,400 A | 10/1997 | Tuch |
| 5,695,516 A | 12/1997 | Fischell et al. |
| 5,716,981 A | 2/1998 | Hunter et al. |
| 5,725,572 A | 3/1998 | Lam et al. |
| 5,733,303 A | 3/1998 | Israel et al. |
| 5,733,925 A | 3/1998 | Kunz et al. |

(Continued)

FOREIGN PATENT DOCUMENTS

EP  04330011 A1  6/1991

(Continued)

OTHER PUBLICATIONS

*Trapidil Inhibits Monocyte Chemoattractant Protein-1 and macrophage Accumulation After Balloon Arterial Injury in Rabbits*, Poon M, Cohen J, Siddiqui Z, et al., Lab Invest. 1999; 79:1369-1375.

(Continued)

*Primary Examiner* — Vy Q Bui

(74) *Attorney, Agent, or Firm* — Fay Sharpe LLP; Brian E. Turung

(57) ABSTRACT

The invention relates to sutures and surgical staples useful in anastomoses. Various aspects of the invention include wound closure devices that use amphiphilic copolymer or parylene coatings to control the release rate of an agent, such as a drug or a biological material, polymerizing a solution containing monomers and the agent to form a coating, using multiple cycles of swelling a polymer with a solvent-agent solution to increase loading, microparticles carrying the agent, biodegradable surgical articles with amphiphilic copolymer coatings, and sutures or surgical staples the deliver a drug selected from the group consisting of triazolopyrimidine, paclitaxol, sirolimus, derivatives thereof, and analogs thereof to a wound site.

41 Claims, No Drawings

U.S. PATENT DOCUMENTS

| | | | |
|---|---|---|---|
| 5,735,871 A | 4/1998 | Sgro | |
| 5,755,781 A | 5/1998 | Jayaraman | |
| 5,772,864 A | 6/1998 | Møller et al. | |
| 5,776,183 A | 7/1998 | Kanesaka et al. | |
| 5,807,944 A | 9/1998 | Hirt et al. | |
| 5,811,447 A | 9/1998 | Kunz et al. | |
| 5,824,045 A | 10/1998 | Alt | |
| 5,824,049 A | 10/1998 | Ragheb et al. | |
| 5,824,077 A | 10/1998 | Mayer | |
| 5,837,313 A | 11/1998 | Ding et al. | |
| 5,843,172 A | 12/1998 | Yan | |
| 5,849,368 A | 12/1998 | Hostettler et al. | |
| 5,853,419 A | 12/1998 | Imran | |
| 5,861,027 A | 1/1999 | Trapp | |
| 5,873,904 A | 2/1999 | Ragheb et al. | |
| 5,879,370 A | 3/1999 | Fischell et al. | |
| 5,911,732 A | 6/1999 | Hojeibane | |
| 5,916,585 A | 6/1999 | Cook | |
| 5,925,065 A | 7/1999 | Totakura et al. | |
| 5,962,620 A | 10/1999 | Reich et al. | |
| 5,964,798 A | 10/1999 | Imran | |
| 5,968,091 A | 10/1999 | Pinchuk et al. | |
| 5,981,568 A | 11/1999 | Kunz et al. | |
| 5,993,972 A * | 11/1999 | Reich et al. | 428/423.1 |
| 6,007,573 A | 12/1999 | Wallace et al. | |
| 6,059,810 A | 5/2000 | Brown et al. | |
| 6,066,325 A | 5/2000 | Wallace | |
| 6,074,659 A | 6/2000 | Kunz et al. | |
| 6,086,863 A | 7/2000 | Ritter et al. | |
| 6,096,070 A | 8/2000 | Ragheb et al. | |
| 6,099,561 A | 8/2000 | Alt | |
| 6,120,536 A | 9/2000 | Ding et al. | |
| 6,120,847 A | 9/2000 | Yang et al. | |
| 6,146,358 A | 11/2000 | Rowe | |
| 6,156,062 A | 12/2000 | McGuinness | |
| 6,156,373 A | 12/2000 | Zhong et al. | |
| 6,162,247 A | 12/2000 | Weadock et al. | |
| 6,171,609 B1 | 1/2001 | Kunz | |
| 6,200,337 B1 | 3/2001 | Moriuchi et al. | |
| 6,200,589 B1 | 3/2001 | Kennedy et al. | |
| 6,200,960 B1 | 3/2001 | Khachigian | |
| 6,206,916 B1 | 3/2001 | Furst | |
| 6,221,099 B1 | 4/2001 | Andersen et al. | |
| 6,245,537 B1 | 6/2001 | Williams et al. | |
| 6,258,121 B1 | 7/2001 | Yang et al. | |
| 6,267,987 B1 * | 7/2001 | Park et al. | 424/486 |
| 6,268,390 B1 | 7/2001 | Kunz | |
| 6,273,908 B1 | 8/2001 | Ndondo-Lay | |
| 6,273,913 B1 | 8/2001 | Wright et al. | |
| 6,287,628 B1 | 9/2001 | Hossainey et al. | |
| 6,290,721 B1 | 9/2001 | Heath | |
| 6,299,604 B1 | 10/2001 | Ragheb et al. | |
| 6,306,421 B1 | 10/2001 | Kunz et al. | |
| 6,322,847 B1 | 11/2001 | Zhong et al. | |
| 6,335,029 B1 | 1/2002 | Kamath et al. | |
| 6,346,133 B1 | 2/2002 | Narasimhan et al. | |
| 6,356,600 B1 | 3/2002 | Kirsteins et al. | |
| 6,358,556 B1 | 3/2002 | Ding et al. | |
| 6,358,989 B1 | 3/2002 | Kunz et al. | |
| 6,365,171 B1 | 4/2002 | Kennedy et al. | |
| 6,368,658 B1 | 4/2002 | Schwarz et al. | |
| 6,369,065 B1 | 4/2002 | Chatelain et al. | |
| 6,379,379 B1 | 4/2002 | Wang | |
| 6,379,381 B1 | 4/2002 | Hossainey et al. | |
| 6,391,052 B2 | 5/2002 | Buirge et al. | |
| 6,399,144 B2 | 6/2002 | Dinh et al. | |
| 6,419,692 B1 | 7/2002 | Yang et al. | |
| 6,436,133 B1 | 8/2002 | Furst et al. | |
| 6,440,460 B1 | 8/2002 | Gurny et al. | |
| 6,485,502 B2 | 11/2002 | Don Michael et al. | |
| 6,488,702 B1 | 12/2002 | Besselink | |
| 6,491,938 B2 | 12/2002 | Kunz et al. | |
| 6,515,009 B1 | 2/2003 | Kunz et al. | |
| 6,517,571 B1 | 2/2003 | Brauker et al. | |
| 6,527,802 B1 | 3/2003 | Mayer | |
| 6,528,584 B2 | 3/2003 | Kennedy et al. | |
| 6,530,951 B1 | 3/2003 | Bates et al. | |
| 6,545,097 B2 | 4/2003 | Pinchuk et al. | |
| 6,555,157 B1 | 4/2003 | Hossainey et al. | |
| 6,555,619 B1 | 4/2003 | Kennedy et al. | |
| 6,569,195 B2 | 5/2003 | Yang et al. | |
| 6,569,441 B2 | 5/2003 | Kunz et al. | |
| 6,583,251 B1 | 6/2003 | Chaikof et al. | |
| 6,585,764 B2 | 7/2003 | Wright et al. | |
| 6,599,275 B1 | 7/2003 | Fischer, Jr. | |
| 6,599,928 B2 | 7/2003 | Kunz et al. | |
| 6,607,598 B2 | 8/2003 | Schwarz et al. | |
| 6,623,521 B2 | 9/2003 | Steinke et al. | |
| 6,624,138 B1 | 9/2003 | Sung et al. | |
| 6,641,611 B2 | 11/2003 | Jayaraman | |
| 6,652,575 B2 | 11/2003 | Wang | |
| 6,656,506 B1 | 12/2003 | Wu et al. | |
| 6,656,966 B2 | 12/2003 | Garvey et al. | |
| 6,663,881 B2 | 12/2003 | Kunz et al. | |
| 6,669,502 B1 | 12/2003 | Bernhart et al. | |
| 6,669,718 B2 | 12/2003 | Besselink | |
| 6,695,833 B1 | 2/2004 | Frantzen | |
| 6,709,379 B1 | 3/2004 | Brandau et al. | |
| 6,720,350 B2 | 4/2004 | Kunz et al. | |
| 6,723,120 B2 | 4/2004 | Yan | |
| 6,726,923 B2 | 4/2004 | Iyer et al. | |
| 6,730,064 B2 | 5/2004 | Ragheb et al. | |
| 6,730,349 B2 | 5/2004 | Schwarz et al. | |
| 6,730,699 B2 | 5/2004 | Li et al. | |
| 6,734,194 B2 | 5/2004 | End et al. | |
| 6,743,805 B2 | 6/2004 | End et al. | |
| 6,749,554 B1 | 6/2004 | Snow et al. | |
| 6,753,071 B1 | 6/2004 | Pacetti | |
| 6,759,431 B2 | 7/2004 | Hunter et al. | |
| 6,764,505 B1 | 7/2004 | Hossainy et al. | |
| 6,770,729 B2 | 8/2004 | Van Antwerp | |
| 6,774,278 B1 | 8/2004 | Ragheb et al. | |
| 6,780,849 B2 | 8/2004 | Herrmann et al. | |
| 6,783,793 B1 | 8/2004 | Hossainy et al. | |
| 6,790,218 B2 | 9/2004 | Jayaraman | |
| 6,808,536 B2 | 10/2004 | Wright et al. | |
| 7,226,467 B2 * | 6/2007 | Lucatero et al. | 606/213 |
| 2001/0014717 A1 | 8/2001 | Hossainy et al. | |
| 2002/0004101 A1 | 1/2002 | Ding et al. | |
| 2002/0013275 A1 | 1/2002 | Kunz et al. | |
| 2002/0032414 A1 | 3/2002 | Ragheb et al. | |
| 2002/0051730 A1 | 5/2002 | Bodnar et al. | |
| 2002/0054900 A1 | 5/2002 | Kamath et al. | |
| 2002/0055759 A1 | 5/2002 | Shibuya | |
| 2002/0071902 A1 | 6/2002 | Ding et al. | |
| 2002/0082679 A1 | 6/2002 | Sirhan et al. | |
| 2002/0091433 A1 | 7/2002 | Ding et al. | |
| 2002/0095133 A1 | 7/2002 | Gillis et al. | |
| 2003/0026840 A1 | 2/2003 | Plank et al. | |
| 2003/0028243 A1 | 2/2003 | Bates et al. | |
| 2003/0028244 A1 | 2/2003 | Bates et al. | |
| 2003/0036794 A1 | 2/2003 | Ragheb et al. | |
| 2003/0040760 A1 | 2/2003 | Hnojewyj et al. | |
| 2003/0040790 A1 | 2/2003 | Furst | |
| 2003/0064098 A1 | 4/2003 | Kararli et al. | |
| 2003/0083646 A1 | 5/2003 | Sirhan et al. | |
| 2003/0093141 A1 | 5/2003 | Dimatteo et al. | |
| 2003/0099712 A1 | 5/2003 | Jayaraman | |
| 2003/0199969 A1 | 10/2003 | Steinke et al. | |
| 2003/0216534 A1 | 11/2003 | Chaikof et al. | |
| 2003/0228364 A1 | 12/2003 | Nathan | |
| 2003/0229390 A1 | 12/2003 | Ashton et al. | |
| 2003/0229392 A1 | 12/2003 | Wong | |
| 2003/0229393 A1 | 12/2003 | Kutryk et al. | |
| 2004/0047909 A1 | 3/2004 | Ragheb et al. | |
| 2004/0049265 A1 | 3/2004 | Ding et al. | |
| 2004/0093076 A1 | 5/2004 | White | |
| 2004/0093077 A1 | 5/2004 | White | |
| 2004/0193247 A1 | 9/2004 | Besselink | |
| 2004/0208985 A1 | 10/2004 | Rowan et al. | |
| 2004/0219223 A1 | 11/2004 | Kunz | |
| 2004/0243225 A1 | 12/2004 | Ragheb et al. | |
| 2004/0254608 A1 * | 12/2004 | Huitema et al. | 606/219 |
| 2005/0107870 A1 * | 5/2005 | Wang et al. | 623/1.44 |

FOREIGN PATENT DOCUMENTS

| | | |
|---|---|---|
| EP | 0 836839 A2 | 4/1998 |
| WO | WO 93/16176 | 8/1993 |
| WO | WO 94/07529 | 4/1994 |
| WO | WO 94/16706 | 8/1994 |
| WO | WO 94/26291 | 11/1994 |
| WO | WO 96/25176 | 8/1996 |
| WO | WO 97/10011 | 3/1997 |
| WO | WO 98/17331 | 4/1998 |
| WO | WO 98/43618 | 10/1998 |
| WO | WO 99/18998 | 4/1999 |
| WO | WO 99/49907 | 10/1999 |
| WO | WO 99/56663 | 11/1999 |
| WO | WO 01/01957 | 1/2001 |
| WO | WO 01/17577 | 3/2001 |
| WO | WO 01/45763 | 6/2001 |
| WO | WO 01/97964 | 12/2001 |

OTHER PUBLICATIONS

*The TRAPIST study—A multicentre randomized placebo controlled clinical trial of trapidil for prevention of restenosis after coronary stenting, measured by 3-D intravascular ultrasound*, P.W. Serruys, D.P. Foley, M. Pieper, J.A. de Feyter on behalf of the TRAPIST investigators, European Heart Journal (2001) 22, 1938-1947, doi:10.1053/euhj.2001.2627, available online at http://www.idealibrary.com.

Abstract of *Fast and Reproducible Vascular Neointima Formation in the Hamster Carotid Artery: Effects of Trapidil and Captopril*, Matsuno H, Stassen JM, Hoylaerts MF, Vermylen J, Deckmyn H., Thromb Haemost. Dec. 1995;74(6):1591-6.

*Results of a Meta-Analysis of Trapidil, a PDGF Inhibitor Â' A Sufficient Reason for a Second Look to the Pharmacological Approach to Restenosis*, Serruys PW, Banz K, Darcis T, Mignot A, van Es GA, Schwicker D., J Invasive Cardiol. Oct. 1997;9(8):505-512.

Management of restenosis after Coronary Intervention, Dangas G, Fuster V., Am Heart J. Aug. 1996;132(2 Pt 1):428-36.

*New Aspects in Antithrombotic Therapy—Platelet Inhibitors-*, Terres W, Meinertz T., Herz. Feb. 1996;21(1):1-11.

*A Randomized Comparison of Trapidil (triazolopyrimidine), a Platelet-Derived Growth Factor Antagonist, Versus Aspirin in Prevention of Angiographic Restenosis after Coronary Artery Palmaz-Schatz Stent Implantation*, Galassi AR, Tamburino C, Nicosia A, Russo G, Grassi R, Monaco A, Giuffrida G., Catheter Cardiovasc Interv. Feb. 1999;46(2):162-8.

*Reference Chart Derived From Post-Stent-Implantation Intravascular Ultrasound Predictors of 6-Month Expected Restenosis on Quantitative Coronary Angiography*, P. J. de Feyter, P. Kay, C. Disco, and P. W. Serruys, Circulation, Oct. 1999; 100: 1777-1783.

Abstract of *Trapidil in Preventing Restenosis After Balloon Angioplasty in the Ather Osclerotic Rabbit*, MW Liu, GS Roubin, KA Robinson, AJ Black, JA Hearn, RJ Siegel, and SB King, 3d Circulation 1990 81: 1089-1093.

Abstract of *Effects of Trapidil (Triazolopyrimidine), a Platelet-Derived Growth Factor Antagonist, in Preventing Restenosis After Percutaneous Transluminal Coronary Angioplasty*, Okamoto S, Inden M, Setsuda M, Konishi T, Nakano T, Am Heart J. Jun. 1992; 123(6):1439-44.

Abstract of *Trapidil (triazolopyrimidine), A Platelet-Derived Growth Factor Antagonist, Reduces Restenosis After Percutaneous Transluminal Coronary Angioplasty. Results of the Randomized, Double-Blind STARC Study. Studio Trapidil Versus Aspirin Nella Restenosi Coronarica*, A Maresta, M Balducelli, L Cantini, A Casari, R Chioin, M Fabbri, A Fontanelli, PA Monici Preti, S Repetto, and S De Serv, Circulation, Dec. 1994; 90: 2710-2715.

Abstract of *The Trapidil Restenosis Trial (STARC study): Background, Methods and Clinical Characteristics of the Patient Population*, Maresta A, Balducelli M, Cantini L, Casari A, Chioin R, Fontanelli A, Monici Preti PA, Repetto S, Raffaghello S.,Clin Trials Metaanal. Apr. 1994,29(1):31-40.

Abstract of *Pharmacological Properties of Trapidil: Comparison with Other Coronary Vasodilators*, Ohnishi H, Kosuzume H, Yamaguchi K, Sato M, Umehara S, Funato H, Itoh C, Suzuki K, Kitamura Y, Suzuki Y, Itoh R., Nippon Yakurigaku Zasshi. Sep. 1980; 76(6):495-503.

Abstract of *Effects of Trapidil on Thromboxane A2-induced Aggregation of Platelets, Ischemic Changes in Heart and Biosynthesis of Thromboxane A2*, Ohnishi H, Kosuzume H, Hayashi Y, Yamaguchi K, Suzuki Y, Itoh R., Prostaglandins Med. Mar. 1981;6(3):269-81.

Abstract of *Antithrombotic Activity and the Mechanism of Action of Trapidil (Rocornal)*, Suzuki Y, Yamaguchi K, Shimada S, Kitamura Y, Ohnishi H., Prostaglandins Leukot Med. Dec. 1982;9(6):685-95.

Abstract of *Suppression of Fibroblast Proliferation In Vitro and of Myointimal Hyperplasia In Vivo by the Triazolopyrimidine, Trapidil*, Tiell ML, Sussman II, Gordon PB, Saunders RN, Artery. 1983;12(1)33-50.

*Influence of Cardiovascular Drugs on Platelet Aggregation*, Forster W, Block HU, Giessler C, Heinroth I, MentzP,Ponicke K, Rettkowski W, Zehl U., : Adv Myocardiol. 1983;4:539-47.

Trapidil in Preventing Restenosis After Balloon Angioplasty in the Atherosclerotic Rabbit, Liu, et al., *Circulation*, vol. 81, No. 3, Mar. 1990.

DNA Delivery from Polymer Matrices for Tissue Engineering, Shea, et al., *Nature Biotechnology*, vol. 17, Jun. 1999.

Polymeric System for Dual Growth Factor Delivery, Richardson, et al., *Nature Biotechnology*, vol. 19, Nov. 2001.

Controlled Growth Factor Release from Synthetic Extracellular Matrices, Lee, et al., *Nature*, vol. 408, Dec. 21/28, 2000.

*Progress in Cardiovascular Disease*, Sonnenblick, et al., Sep./Oct. 1996.

*USCI PE Plus Peripheral Balloon Dilatation Catheter* brochure.

\* cited by examiner

SUTURES AND SURGICAL STAPLES FOR ANASTAMOSES, WOUND CLOSURES, AND SURGICAL CLOSURES

PRIORITY

This application is a continuation-in-part of provisional application No. 60/567,702, filed May 3, 2004 and of application Ser. No. 10/209,591, filed Jul. 31, 2002.

FIELD OF THE INVENTION

The present invention relates generally to the field of medicine and more particularly relates to polymer and drug coated sutures and surgical staples.

BACKGROUND OF THE INVENTION

An important consideration in performing surgery is the "hand" or "feel" of the suture being used to close wounds. These are reflected by the knot "tie-down" and "run-down" characteristics of the suture. Tie-down characteristics refer to the ease with which a surgeon can tie a knot, and the ability of the suture to remain knotted without unraveling. Run-down characteristics refer to the ability of a surgeon to make one or more "throws" of a knot in the suture and have it run down a suture to the knot site. Generally, these characteristics relate to the lubricity and stiffness of the suture; lubricity facilitates the tying of a knot whereas stiffness makes tying a tight knot more difficult and increases the probability of kinking of the suture and/or unraveling of the knot.

Multifilament sutures, such as braided or twisted sutures, have better softness and flexibility than monofilament sutures and can be more easily knotted. However, multifilament sutures can have a rougher surface or more "grabbiness" than monofilament sutures and significant dead space (interstices) between filaments. The dead space can be reduced by impregnating the suture with a filler material. Filler material can help lubricate the suture fibers and enhance flexibility.

Many sutures materials are bio-absorbable and susceptible to hydrolysis. For these sutures, extreme care must be taken to rigorously exclude moisture during storage. For example, the strength of polyglycolic acid sutures undergoes significant deterioration during long term storage in the presence of even small amounts of water. Prior to packaging, these sutures are heated for an extended period to remove essentially all the water. They are then promptly packaged in a moisture free environment.

Due to various drawbacks in this approach, other approaches to improving the storage stability of absorbable sutures have been proposed. For example, it has been proposed to use filler material to improve the storage stability of multifilament sutures. In one example, the filler material contains at least one water-soluble liquid polyhydroxy compound and/or ester thereof. It has also been suggested that the polyhydroxy compounds can improve the hand of the suture and are capable of dissolving a variety of useful drugs and can be used as vehicles to deliver drugs to a wound site.

At present, many biocompatible polymers are known. For example, poly(ethylene glycol) (PEG) is a water-soluble polymer showing excellent biocompatibility and has been frequently used in biomedical applications. Similarly, polysiloxanes are widely used in the biomedical field and have been the subject of intense study both in the academic field as well as in industry.

Amphiphilic polymer networks have also been identified as potentially useful biomaterials. Amphiphilic polymer networks are co-continuous assemblages of hydrophilic and hydrophobic polymer chains that are able to swell in both hydrophilic solvents (e.g., water) and hydrophobic solvents (e.g., a liquid hydrocarbon). Because these materials swell in water, they generally fall into a class of compounds known as "hydrogels".

The first amphiphilic membranes for biomaterials were developed over a decade ago. These were networks of hydrophilic polymers with the hydrophobic crosslinking agent, di-methacryl-telechelic polyisobutylene (MA-PIB-MA). Synthesis was accomplished by living carbocationic polymerization, which involves free radical copolymerization and can use a variety of inexpensive, commercially available monomers, for example, N-dimethylaminoethyl methacrylate and dimethyl acrylamide.

Kennedy, U.S. Pat. No. 4,486,572 discloses the synthesis of styryl-telechelic polyisobutylene and amphiphilic networks comprising the copolymerization product of the styryl-telechelic polyisobutylene with vinyl acetate or N-vinyl-2-pyrollidone. Kennedy, U.S. Pat. No. 4,942,204 discloses an amphiphilic copolymer network swellable in both water and n-heptane but insoluble in either, comprising the reaction product of an acrylate or methacrylate of a dialkylaminoalkyl with a hydrophobic bifunctional acryloyl or methacryloyl capped polyolefin. The preferred embodiment disclosed is an amphiphilic network having been synthesized by the free-radical copolymerization of a linear hydrophobic acrylate (A-PIB-A) or methacrylate capped polyisobutylene (MA-PIB-MA) with 2-(dimethylamino)ethyl methacrylate (DMAEMA). In a continuation-in-part to U.S. Pat. No. 4,942,204, Ivan et al. U.S. Pat. No. 5,073,381 discloses various amphiphilic copolymer networks that are swellable in water and n-heptane that comprise the reaction product of a hydrophobic linear acryloyl- or methacryloyl-capped polyolefin and a hydrophilic polyacrylate or polymethacrylate, such as N,N-dimethylacrylamide (DMAAm) and 2-hydroxyethylmethyl methacrylate (HEMA).

Hirt, U.S. Pat. No. 5,807,944 discloses a copolymer of controlled morphology comprising at least one oxygen permeable polymer segment and at least one ion permeable polymer segment, wherein the oxygen permeable segments and the ion permeable segments are linked together through a non-hydrolysable bond. The oxygen-permeable polymer segments are selected from polysiloxanes, perfluoroalkyl ethers, polysulfones, and other unsaturated polymers. The ion permeable polymers are selected from cyclic imino ethers, vinyl ethers, cyclic ethers, including epoxides, cyclic unsaturated ethers, N-substituted aziridines, beta-lactones, beta-lactanes, ketene acetates, vinyl acetates and phosphoranes.

U.S. application Ser. No. 09/433,660 discloses an amphiphilic network comprising the reaction product of hydrophobic crosslinking agents and hydrophilic monomers wherein the hydrophobic crosslinking agents are telechelic three-arm polyisobutylenes having acrylate or methacrylate end caps and wherein the hydrophilic monomers are acrylate or methacrylate derivatives.

Sutures and surgical staples can be used for anastamoses. Anatomoses involves the joining of veins or arteries. During anastamoses, damage to the neointimal layers of the veins and arteries (the interior layers) occurs through physical manipulation and the device used for joining. This damage affects the healing process and can result in the failure of an arterial or veinous graft. There remains a long felt need for more successful anastamoses procedures.

SUMMARY OF THE INVENTION

The following presents a simplified summary in order to provide a basic understanding of some aspects of the invention. This summary is not an extensive overview of the invention. It is intended neither to identify key or critical elements of the invention nor to delineate the scope of the invention. Rather, the primary purpose of this summary is to present some concepts of the invention in a simplified form as a prelude to the mere detailed description that is presented later.

One aspect of the invention relates to a suture or surgical staple having a surface with a coating comprising an amphiphilic copolymer that includes both hydrophobic and hydrophilic polymer chains. An amphiphilic copolymer coating according to the invention can improve the tie-down and run-down characteristics of a suture. An amphiphilic copolymer coating can also serve as a carrier for a very broad range of substances. The release rate of the substance can be controlled, for example, through the length of the polymer chains, their ratio, or their degree of crosslinking.

Another aspect of the invention relates to a suture or surgical staple, a surface of which has a coating comprising either parylene or an amphiphilic polymer. The polymer controls the release rate of an agent having a function selected from the group consisting of preventing scarring, preventing infection, or preventing an adverse reaction to a procedure for installing the device. The release rate of the agent can be adjusted by varying the thickness of a parylene coating.

A further aspects of the invention relates to manufacturing an amphiphilic polymer-coated suture or surgical staple. One embodiment involves polymerizing a solution containing monomers and an agent. Another embodiment involves increasing the loading of an agent through multiple cycles of swelling the polymer with a solvent-agent solution and evaporating at least some of the solvent between cycles.

A further aspect of the invention relates to a suture or surgical staple wherein microparticles, especially microparticles of parylene or amphiphilic copolymers, are used as carriers for drugs. The microparticles can be trapped in interstices of the device or formed in a coating over the device.

A further aspect of the invention relates to a biodegradable surgical article with an amphiphilic copolymer coating. The amphiphilic copolymer coating can exclude moisture or otherwise prolong the storage stability of the surgical article.

A still further aspect of the invention provides sutures or surgical staples for anastomoses. The sutures or surgical staples deliver a drug selected from the group consisting of triazolopyrimidine, paclitaxol, sirolimus, derivatives thereof, and analogs thereof to the wound site. The release rate of the drug can be controlled by a polymer coating the suture or surgical staple. The drug can mitigate the adverse effects of damage to a neointimal later of a vessel caused by anastomoses.

To the accomplishment of the foregoing and related ends, the following description and annexed drawings set forth in detail certain illustrative aspects and implementations of the invention. These are indicative of but a few of the various ways in which the principles of the invention may be employed. Other aspects, advantages and novel features of the invention will become apparent from the following detailed description of the invention when considered in conjunction with the drawings.

DETAILED DESCRIPTION OF THE INVENTION

An exemplary surgical article according to one aspect of the invention includes a suture or surgical staple, an effective amount of an agent, and a polymer controlling the release rate of the agent. Preferably, the polymer is either an amphiphilic copolymer or a parylene. A suture according to the invention can have superior tie-down and run-down characteristics. A suture or surgical staple according to the invention can also provide a versatile platform for drug delivery. The polymer can have a high degree of bio- and hemo-compatibility. Release rates can be controlled as needed through variations in composition, loading, layering, thickness, and/or cross-linking. The agent can be carried or encapsulated by the polymer. Where the polymer encapsulates the agent, the agent can be adsorbed into or coated over the suture or surgical staple.

A suture or surgical staple can be of any suitable material. The material can be natural or synthetic, biostable or bioabsorbable. Examples of polymeric biostable synthetic materials include polypropylene, nylon, polyamide, polyethylene, polyesters (such as polyethylene terephthalate), polytetrafluoroethylene, polybutester, segmented polyether-ester block copolymers, and blends and copolymers thereof. Examples of non-polymeric biostable synthetic materials include carbon fibers, steel fibers and other biologically acceptable inorganic fibrous materials. Example of bioabsorbable synthetic materials include poly(lactide-co-glycolide) (PLGA), polyglycolide, polylactide, polyglactic, polyglyconate, polydioxanone, polyhydroxybutyrate, polycaprolactone, polyorthoesters, polyesteramides, copolyoxalates, polycarbonate (e.g. trimethylene carbonate), polyanhydrides, poly(glutamic-co-leucine), polysaccharide, and blends and copolymers thereof. Examples of biostable natural materials include silk, cotton, and linen. An example of a bioabsorbable natural material is catgut (a collagen based material).

A suture can be a single filament strand, i.e., a monofilament suture, or a multifilament strand. Multifilament structures include, for example, braided and twisted structures. The suture may be of any suitable thickness, including for example 11–0, 10–0, 9–0, 8–0, 7–0, 6–0, 5–0, 4–0, 3–0, 2–0, 1–0, 0, 1, 2, 3, 4, and 5. Preferably the thickness is in the range from 3–0 to 0.

Amphiphilic copolymer coatings provide a versatile substance delivery platform. Versatility is important in view of the need to conduct extensive testing prior to introducing any new material into the human body. A suture or surgical staple according to this aspect of the invention can easily, and with minimal testing, be adapted to implement advances in suture or surgical staple design and treatments.

Various definitions of amphiphilic polymer are used in the literature. For purposes of the present disclosure, however, an amphiphilic polymer is a copolymer that includes both hydrophobic and hydrophilic polymer chains and is able to swell in both hydrophilic solvents (e.g., water) and hydrophobic solvents (e.g., n-heptane). This definition excludes, for example, a simple poly(ethylene glycol) polymer, which some have characterized as amphiphilic in view of its intermediate hydrophilicity.

Amphiphilic block copolymers include polymers having hydrophobic polymer chains crosslinked by hydrophilic polymer chains, polymers having hydrophilic polymer chains crosslinked by hydrophobic polymer chains, polymers having hydrophobic and hydrophilic polymer chains crosslinked by a crosslinking agent, and polymers in which hydrophobic and hydrophilic chains link end to end. Amphiphilic graft copolymers include polymers having a hydrophilic backbone to which hydrophobic chains are attached and polymers having a hydrophobic backbone to which hydrophilic chains are attached. As the terms are used here, a graft copolymer is not, in general, a block copolymer.

The assemblages of polymer chains are generally random. Preferably, the polymer chains form a continuous network through either physical or chemical crosslinking. Physical crosslinking refers, for example, to bonding that occurs through aggregation of groups of hydrophobic segments, which results from their mutual attraction.

The monomers from which block copolymers are made generally include polymer chains. Under the terminology used here, these monomers may be referred to as macro-monomers. Likewise, the corresponding elements in the formed block copolymer can be referred to as macro-mers.

A hydrophobic polymer chain can be, for example, a polyolefin, preferably an olefin having 4 to about 12 carbon atoms as in poly(isobutylene), or a polysiloxane, such as poly(dimethylsiloxane). A hydrophilic polymer chain can be, for example, a poly(alkylene glycol), such as polyethylene glycol, a polyacrylate, such as polymers of methacrylate, 2-hydroxyethyl methylmethacrylate, or an aminoalkyl acrylate, such as N,N-dimethylacrylamide.

A preferred amphiphilic block copolymer network comprises macromolecular mers of polyethylene glycol (PEG), poly(isobutylene) (PIB), and poly(dimethylsiloxane) (PDMS). The polymer network can be synthesized by hydrosilation of allyl-terminated macromolecular monomers with pentamethylcyclopentasiloxane in toluene. The pore size of this network can be controlled by controlling the molecular weight of the hydrophilic macro-monomers. The strength can be controlled by the lengths of the hydrophobic macro-monomers and by the crosslink density. PDMS is oxyphilic and enhances transport of oxygen and related substances through the network.

More generally, macro-monomers, each a hydrophilic or hydrophobic polymer chain with functional end caps, can be polymerized together to form an amphiphilic block copolymer network. Suitable end caps include, for example, organic polyisocyanates, such as tolyene diisocyanate and diphenylmethane diisocyanate, acrylate, methacrylate and styryl groups. Block copolymers networks can also be generated by polymerizing polymer chains with monomers, for example, methacrylol capped PIB with dimethylaminoethyl methacrylate.

The solubility difference between hydrophobic and hydrophilic monomers can be an issue during synthesis of amphiphilic block copolymers. One method of managing this issue is to use a removable blocking agent to make a hydrophobic monomer temporarily hydrophilic or a hydrophilic monomer temporarily hydrophobic. For example a hydrophobic tertiary amine or amide can be made hydrophilic with a protonating blocking agent. For another example, a hydrophilic methacrylate can be made hydrophobic by the blocking agent trimethylsilyl chloride. The trimethylsilyl chloride can be removed by swelling the polymer in a 5% hydrochloric acid solution.

An exemplary process for coating a suture with an amphiphiic copolymer/agent composition comprises spooling the suture through a series of stages. The stages may include, for example, a stage in which the suture passes through a solution containing monomers and the agent, a stage where the monomers are polymerized, a stage where endcaps are removed, a stage where solvent are evaporated, and a stage where the sutures are cut.

Amphiphilic block copolymers as used in the invention are generally biostable. However, bioerodable amphiphilic block copolymers can also be designed. For example, a bioerodable amphiphilic block copolymer can be obtained by copolymerizing, under free radical conditions, styrene-telechelic PIB's with vinyl acetate.

With regard to bioerodable articles, an advantage of the amphiphilic copolymers is the ability to swell the polymer in either hydrophobic or hydrophilic solvents. The feature can be used to load various agent without damaging the article. This property may also be used to remove water without heating the article. Solvents miscible with water, but with lower boiling points, can be used to facilitate water removal. This is particularly valuable in loading biological materials, especially materials that are unstable at higher temperatures, e.g., temperatures over 65° C.

An amphiphilic can deliver many different agents with little or no variation in the polymer composition. For example, an amphiphilic block copolymer network, such as networks comprising PEG, PIB, and PDMS, can be used to deliver with a controlled release rate any of triazolopyrimidine, paclitaxol, and sirolimus on the one hand and any of stem cells, antibodies, genetic materials, and lymphokines on the other.

The polymer can either be formed over an agent-containing material or the polymer be loaded with the agent by any suitable means. One approach is to include the agent with monomers or macro-monomers as they are polymerized together. Another is to dissolve the agent in a solvent and swell the polymer with the solvent. All or part of the solvent can be evaporated and the polymer swelled again to increase the agent loading level.

Amphiphilic copolymer networks can be tailored to provide virtually any desired release rate. Non-soluble amphiphilic block copolymers generally provide release rate kinetics in the range from about 0.4 order to about first order. Within this framework, a particular release rate may be targeted. In one embodiment, the suture or surgical staple releases at least about 10 of the agent within seven days of installation under the skin. Preferably from about 10 to about 90 percent of the drug is released after seven days. In another embodiment, from about 10 to about 90 percent of the drug is release as of six hours after installation, preferably from about 20 to about 60 percent.

A variety of options are available for controlling the release rate of amphiphilic copolymers. The release rate can be varied though any of: the identity of the macro-monomers, the lengths of the macro-monomer chains, the ratios of the macro-monomers, the degree of crosslinking in the copolymer network, the loading of the drug, and the thickness of the amphiphilic polymer coating. Additional release patterns can be obtained by employing multi-layer coatings, which may include layers that are not amphiphilic copolymers. For example, a barrier layer may be formed over the amphiphilic copolymer to slow the release rate. A preferred barrier layer comprises parylene or a derivative thereof.

Alternatively, a parylene coating can be used to control an agent release rate without an amphiphilic polymer coating. A parylene is a polymer based on a di-para-xylene. Typically, each of the xylenes is substituted with one chlorine atom, although other substitutions and greater or lesser numbers of substitutions can be made. A parylene coating can be formed by pyrolyzing the dimers in a vacuum chamber containing the material to be coated. In a typical process, the suture is spooled through a solution containing an agent to be deliver by the suture, then through a drying chamber, and then through a vacuum chamber, where the parylene coating is deposited. By varying the parylene coating thickness, the release rates of a variety of agents can be controlled. A parylene can be used to control the release rate of any of triazolopyrimidine, paclitaxol, and sirolimus, for example.

An agent can be adsorbed into the suture or surgical staple or provided in a coating on the suture or staple over which the parylene coating is formed. This same approach can be used for amphiphilic polymer coatings. The drug diffuses through the coating, whereby the coating controls the release rate.

The polymer coats a surface of a suture or surgical staple. For a suture, the can mean, for example, that lengths of strands making up a suture or a portion of a staple is enclosed by the polymer. Alternatively, this can mean the polymer fills interstices within a strand, suture, or surgical staple (coats internal surfaces). In addition to the processes described above, a coating can be applied to a suture or surgical staple by any suitable means, including for example, spray coating and dip coating, and brush coating.

According to another aspect of the invention, the suture or surgical staple carries a functional amount with of an agent and the polymer controls the release rate of the agent. The function is selected from the group consisting of preventing scarring, preventing infection, or preventing an adverse reaction to a procedure for installing the device.

A suture or surgical staple according to the invention can be used to deliver virtually any agent. The term agent, as used herein, can be a drug, stem cells, antibodies, genetic materials, or lymphokines. Agents that can be delivered according to the invention include, without limitation, hydrophilic compounds, hydrophobic compounds, metal compounds, salts, polymers, antibodies, proteins, nucleic acids, and cells. It is further possible to control the release rate of any of these agents.

Diverse agent may be of interest in connection with sutures or surgical staples, including the following:

antimicrobial agents such as broad spectrum antibiotics (e.g., Gentacmycin sulphate, erythromycin or derivatized glycopeptides);

anticoagulants, including heparin, low molecular weight herapins, hirudin, warfarin, bivalirudin, and Vasoflux;

antithrombotic agents, including argatroban, efegatran, tick anticoagulant peptide, Ppack, HMG-CoA reductase inhibitors, thromboxane A2 receptor inhibitors, endothelium-derived relaxing factor plasminogen activator inhibitor, tissue-type plasminogen activator (tPA), ReoPro, fibrin and fibrin peptide A, chrysalin, D-Phe-ProArg chloromethyl ketone, and glycoprotein IIb/IIIa receptor inhibitors (including, abciximab, eptifibatide, tirofiban, lamifiban, fradafiban, cromafiban, toxifiban, XV454, lefradafiban, klerval, lotrafiban, orbofiban, and xemilofiban)

antiplatelet agents, including aspirin, dipyridamole, apo-dipyridamole, persantine, prostacyclin, ticlopidine, clopidogrel, cromafiban, and cilostazol;

antiproliferative agents, including triazolopyrimidine (Trapidil), paclitaxel (Taxol), tranilast (Rizaben), Rapamycin (sirolimus), tacrolimus, angiopeptin, butyrate, ceramide, ciprostene, cultrazine, cyclosporine, EGF-genistein, fucoidans, halofuginone, lioprost, ketaserine, predisone, dipyridamole, 17-beta-estradiol, suramin, nitric oxide donors (including FK409, linsidomine, and molsidomine), phytoestrogens, colchine, probucol, terbinafine, etoposide, doxorubicine, beraprost sodium, Resten-NG, actinomycin D, phosphorylcholine, Batimastat, and calcium channel blockers (including, amlodipine, verapamil, diltiazem HCL, and nifedipine);

anti-inflammatory agents, including dipyridamole, and glucocorticoids (including betamethazone, rosiglitazone, and dexamethazone);

lipid-lowering drugs, including omega-3 fatty acids, prostaglandin $I_2$, prostaglandin E1, pravastatin, lovastatin, cerivastatin, fluvastatin, and simvastatin;

specific growth factor antagonists, including lanreotide;

antioxidants, including alpha-tocopherol, beta-carotene, and probucol;

genetic materials, including those carried by viral vectors, plasmids, and lipid-based carriers (including, antisense oligonucleotides such as AVI-2221, INX-3280, RestenASE), ribosymes, and cytochalasin B;

angiogenic growth factors, including platelet derived growth factors alpha and beta;

antihypertension drugs, including angiotensin converting enzyme inhibitors and angiotensin II receptor antagonists (including captopril, quinapril, cilazapril, losartan, and valsartan)

radioactive compounds, including metal salts;

lymphokines including (IL)-1, -2, -3, and -4, as well as colony stimulating factors such as G-CSF, GM-CSF, and M-CSF.

Most of these agents have analogs and derivative that are also of interest. Analogs and derivatives include minor alterations in structure and substitutions or additions of atoms or functional groups that do not alter, except perhaps by degree, the primary mechanism of action. For example paclitaxel derivatives include, without limitation, taxotere, baccatin, 10-deacetyltaxol, 7-xylosyl-10-deacetyltaxol, cephalomannine, 10-deacetyl-7-epitaxol, 7 epitaxol, 10-deacetylbaccatin III, and 10-deacetylcephaolmannine.

One aspect of the present invention is to provide an agent on a suture or surgical staple that mitigates damage to the neointimal layer that occurs during anastomoses. The agent can be, for example, triazolopyrimidine, paclitaxel, sirolimus, stem cells, antibodies, genetic materials, or lymphokines. A preferred agent is triazolopyrimidine.

The agent can remain in the surgical article, as when the agent is a radiation source. More generally, however it is preferred that the agent be released by the article. In one embodiment, the agent is of a type that can absorb and be stored in living tissues.

Local drug delivery through a suture or surgical staple coating often allows the use of higher drug concentrations in those locations where the drug is needed than could safely be achieved with system wide delivery. Nonetheless, there can be synergy between suture-based delivery and system-wide delivery. Thus, in one embodiment, treatment with an agent-delivering suture or surgical staple according to the invention is combined with oral, intravenous, or topical dosage of the same agent.

In addition to a suture or surgical staple coating, an amphiphilic copolymer or a parylene can be used to form microparticles. Such microparticles can also carry and deliver at a controlled rate a wide range of agents. Microparticles have a size range from about 10 nanometers to about 200 micrometers, preferably from about 50 nm to about 1 micrometer.

One aspect of the invention relates to the use of microparticles, especially amphiphilic copolymer microparticles or parylene microparticles, to carry an agent on a suture or surgical staple. The microparticles can be distributed in a coating on the exterior of the suture or surgical staple or in interstices of the suture or surgical staple. Interstices can be, for example, spaces between filaments or pores in a structure. A coating can be a polymer, either biostable or bioerodable. In a preferred embodiment, the coating containing the microparticles is a hydrogel. A hydrogel can be synthetic polymer, such as polymalic acid, polyamino acids, polyacrylic acids, polyalkylene glycol (e.g., polyethylene glycol), polyalkyene oxide (e.g. polyethylene oxide), polyvinylpyrrolidone, polyester, polyvinyl alcohols, and hydrophilic polyurethanes, polyglutarunic acid, poly 2-hydroxyethyl methacrylate (PHEMA). Additional examples of hydrogels include collagen, NO-carboxymethyl chitosan (NOCC), albumin, gelatin, starch, celluloses, dextran, polymalic acid, polyamino acids and their co-polymers or lightly cross-linked forms, polysaccharides and their derivatives, sodium alginate, karaya gum, gelatin, guar gum, agar, algin, carrageenans, pectin, locust bean gums, xanthan, starch-based gums, hydroxyalkyl and ethyl ethers of cellulose, sodium carboxymethylcellulose.

The invention has been shown and described with respect to certain aspects, examples, and embodiments. While a particular feature of the invention may have been disclosed with respect to only one of several aspects, examples, or embodiments, the feature may be combined with one or more other features of the other aspects, examples, or embodiments as may be advantageous for any given or particular application. Furthermore, to the extent that the term "includes" is used in either the detailed description or the claims, the term is intended to be inclusive in the manner of the term "comprising."

The invention claimed is:

1. A surgical article, comprising:
   a surgical joining device selected from the group consisting of sutures and surgical staples said surgical joining device formed of a biostable or bioabsorbable polymer;
   a coating over a surface of said device, said coating including amphiphilic copolymer; and
   an agent carried by said coating or said device such that said coating controls a release rate of said agent;
   wherein said agent present in a functional amount with a function selected from the group consisting of preventing scarring, preventing infection, or preventing an adverse reaction to a procedure for installing said device; and
   said amphiphilic copolymer comprising a network including both hydrophobic and hydrophilic polymer chains that are able to swell in both hydrophobic and hydrophilic solvents, said hydrophobic polymer chain including polyolefin or polysiloxane, said hydrophilic polymer chain including poly(alkylene glycol), polyacrylate, or aminoalkyl acrylate, said network including PEG, PIB, PDMS, and combinations thereof.

2. The surgical article of claim 1, wherein the device carries a functional amount of the agent.

3. The surgical article of claim 1, wherein the polymer carries a function amount of the agent.

4. The surgical article claim 1, wherein the agent is a drug selected from the group consisting of triazolopyrimidine, derivatives of triazolopyrimidine, paclitaxol, derivatives of paclitaxol, sirolimus, and derivatives of sirolimus.

5. The surgical article of claim 4, wherein the agent is GM-CSF.

6. The surgical article as defined in claim 4, including microparticles in said coating, said microparticles carrying an effective amount of said agent, said microparticles including hydrogel or parylene, said microparticles having a size of about 10 nm to 200 µm, said microparticles located in interstices in said surgical joining device or in said coating over said outer surface of said surgical joining device.

7. The surgical article of claim 1, wherein the agent is selected from the group consisting of stem cells, antibodies, genetic materials, and lymphokines.

8. The surgical article of claim 7, wherein the agent is stem cells.

9. The surgical article of claim 1, wherein the polymer is an amphiphilic copolymer that can be redesigned by changes selected from the group consisting of varying lengths of the hydrophobic and hydrophilic polymer chains, ratios between chains, and/or extent of cross-linking to carry any of the drugs triazolopyrimidine, paclitaxol, and sirolimus and to control the release rate of the drug whereby at least 10 percent of the drug releases within seven days of installation of the surgical article beneath the skin of a mammal.

10. The surgical article of claim 1, wherein the polymer is an amphiphilic copolymer that can be redesigned by changes selected from the group consisting of varying lengths of the hydrophobic and hydrophilic polymer chains, ratios between chains, and/or extent of cross-linking to carry any agent selected from a group consisting of a stem cell, an antibody, a genetic material, and a lymphokine and to control the release rate of the agent whereby at least 10 percent of the agent releases within seven days of installation of the surgical article beneath the skin of a mammal.

11. The surgical article of claim 1, wherein the amphiphilic copolymer comprises poly(alkylene glycol) chains and poly (olefin) chains.

12. The surgical article of claim 11, wherein the amphiphilic copolymer further comprises polysiloxane chains.

13. The surgical article as defined in claim 12, including microparticles in said coating, said microparticles carrying an effective amount of said agent, said microparticles including hydrogel or parylene, said microparticles having a size of about 10 nm to 200 µm, said microparticles located in interstices in said surgical joining device or in said coating over said outer surface of said surgical joining device.

14. The surgical article as defined in claim 13, wherein said microparticles include parylene.

15. The surgical article as defined in claim 13, wherein said microparticles include hydrogel, said hydrogel including a compound selected from the group consisting of polymalic acid, polyamino acids, polyacrylic acids, polyalkylene glycol, polyalkyene oxide, polyvinylpyrrolidone, polyester, polyvinyl alcohols, hydrophilic polyurethanes, polyglutarunic acid, poly 2-hydroxyethyl methacrylate, collagen, NO-carboxymethyl chitosan, albumin, gelatin, starch, celluloses, dextran, polymalic acid, polyamino acids, polysaccharides, sodium alginate, karaya gum, gelatin, guar gum, agar, algin, carrageenans, pectin, locust bean gums.

16. The surgical article as defined in claim 11, wherein said surgical joining device is a polymeric suture; and said amphiphilic copolymer coating on a surface of said polymeric suture.

17. The surgical article as defined in claim 16, including microparticles in said coating, said microparticles carrying an effective amount of said agent, said microparticles including hydrogel or parylene, said microparticles having a size of about 10 nm to 200 µm, said microparticles located in interstices in said surgical joining device or in said coating over said outer surface of said surgical joining device.

18. The surgical article as defined in claim 17, wherein said surgical joining device is bioabsorbable.

19. The surgical article of claim 1, wherein the surgical article once installed under the skin of a mammal releases at least 10 percent of the agent within seven days.

20. A method of treating a living human being, comprising, treating a patient with a surgical article according to claim 1; and administering the agent to the patient either orally, intravenously, or topically.

21. A surgical staple according to claim 1, wherein the device is a surgical staple.

22. The surgical article as defined in claim 1, including microparticles in said coating, said microparticles carrying an effective amount of said agent, said microparticles including hydrogel or parylene, said microparticles having a size of about 10 nm to 200 µm, said microparticles located in interstices in said surgical joining device or in said coating over said outer surface of said surgical joining device.

23. The surgical article as defined in claim 22, wherein said microparticles include parylene.

24. A surgical article, comprising:
a surgical joining device selected from the group consisting of sutures and surgical staples, said surgical joining device formed of a biostable or bioabsorbable polymer;
microparticles carried by the device, said microparticles including a hydrogel, said microparticles have a size of about 10 nm to 200 μm, said hydrogel including a compound selected from the group consisting of polymalic acid, polyamino acids, polyacrylic acids, polyalkylene glycol, polyalkyene oxide, polyvinylpyrrolidone, polyester, polyvinyl alcohols, hydrophilic polyurethanes, polyglutarunic acid, poly 2-hydroxyethyl methacrylate, collagen, NO-carboxymethyl chitosan, albumin, gelatin, starch, celluloses, dextran, polymalic acid, polyamino acids, polysaccharides, sodium alginate, karaya gum, gelatin, guar gum, agar, algin, carrageenans, pectin, locust bean gums, xanthan, starch-based gums, hydroxyalkyl, ethyl ethers of cellulose, and sodium carboxymethylcellulose; and
an effective amount of an agent carried by said microparticles;
wherein said agent has an effect selected from the group consisting of preventing scarring, preventing infection, or preventing an adverse reaction to a procedure for installing the device; and
said microparticles located in interstices in said device or in a coating over a surface of said device.

25. The device of claim 24, wherein the microparticles are carried by a coating over the device.

26. The device of claim 25, wherein the coating comprises collagen.

27. A suture according to claim 24, wherein the surgical joining device is a suture; and the suture comprises multiple filaments and said microparticles are trapped between said filaments.

28. The device of claim 24, wherein the agent is selected from the group consisting of triazolopyrimidine, derivatives of triazolopyrimidine, paclitaxol, derivatives of paclitaxol, sirolimus, and derivatives of sirolimus.

29. The device of claim 28, wherein the agent is triazolopyrimidine, a derivative thereof.

30. The device of claim 29, wherein the agent includes GM-CSF.

31. The device of claim 24, wherein the agent is selected from the group consisting of stem cells, antibodies, genetic materials, and lymphokines.

32. The device of claim 31, wherein the agent is stem cells.

33. A surgical article comprising:
a surgical joining device selected from the group consisting of sutures and surgical staples, said surgical joining device formed of a biostable or bioabsorbable polymer;
a coating over an outer surface of said device, said coating including amphiphilic copolymer, said amphiphilic copolymer comprising a network including both hydrophobic and hydrophilic polymer chains that are able to swell in both hydrophobic and hydrophilic solvents, said hydrophobic polymer chain including polyolefin or polysiloxane, said hydrophilic polymer chain including poly(alkylene glycol), polyacrylate, or aminoalkyl acrylate, said network including PEG, PIB, PDMS, and combinations thereof;
an agent located in interstices in said device or carried by said coating, said coating controlling a release rate of said agent from said surgical joining device whereby at least 10 percent of said agent releases from said surgical joining device within seven days of installation of said from said surgical joining device beneath skin of a mammal, said agent present in a functional amount with a function selected from the group consisting of preventing scarring, preventing infection, or preventing an adverse reaction to a procedure for installing said device; and,
microparticles included in said coating, said microparticles carrying an effective amount of said agent, said microparticles including hydrogel or parylene, said microparticles having a size of about 10 nm to 200 μm, said microparticles located in interstices in said surgical joining device or in said coating over said outer surface of said surgical joining device.

34. The surgical article as defined in claim 33, wherein said amphiphilic copolymer includes poly(alkylene glycol) chains, poly(olefin) chains and polysiloxane chains.

35. The surgical article as defined in claim 34, wherein said agent includes a compound selected from the group consisting of antimicrobial agent, anticoagulant, antithrombotic agent, antiplatelet agent, antiproliferative agent, anti-inflammatory agent, lipid-lowering drug, specific growth factor antagonist, antioxidant, genetic material, angiogenic growth factor, antihypertension drug, radioactive compound, lymphokine, and colony stimulating factor.

36. The surgical article as defined in claim 35, wherein said agent includes a compound selected from the group consisting of triazolopyrimidine, derivatives of triazolopyrimidine, paclitaxol, derivatives of paclitaxol, sirolimus, and derivatives of sirolimus.

37. The surgical article as defined in claim 35, wherein said surgical joining device is bioabsorbable.

38. The surgical article as defined in claim 33, wherein said amphiphilic copolymer includes macromolecular mers of polyethylene glycol, poly(isobutylene), and poly(dimethylsiloxane).

39. The surgical article as defined in claim 33, wherein said agent includes a compound selected from the group consisting of antimicrobial agent, anticoagulant, antithrombotic agent, antiplatelet agent, antiproliferative agent, anti-inflammatory agent, lipid-lowering drug, specific growth factor antagonist, antioxidant, genetic material, angiogenic growth factor, antihypertension drug, radioactive compound, lymphokine, and colony stimulating factor.

40. The surgical article as defined in claim 39, wherein said agent includes a compound selected from the group consisting of triazolopyrimidine, derivatives of triazolopyrimidine, paclitaxol, derivatives of paclitaxol, sirolimus, and derivatives of sirolimus.

41. The surgical article as defined in claim 33, wherein said surgical joining device is bioabsorbable.

* * * * *